(12) United States Patent
Ashraf et al.

(10) Patent No.: US 8,518,446 B2
(45) Date of Patent: Aug. 27, 2013

(54) COATED TABLET FORMULATIONS AND USES THEREOF

(75) Inventors: Muhammad Ashraf, Elmwood, NJ (US); Mainuddin Mahmud, Oak Ridge, NJ (US); Chimanlall Goolcharran, East Lyme, CT (US); Krishnendu Ghosh, Sparkill, NY (US); Arwinder Singh Nagi, Moorpark, CA (US)

(73) Assignee: Wyeth LLC, Madison, NJ (US)

( * ) Notice: Subject to any disclaimer, the term of this patent is extended or adjusted under 35 U.S.C. 154(b) by 15 days.

(21) Appl. No.: 12/940,808

(22) Filed: Nov. 5, 2010

(65) Prior Publication Data

US 2011/0111018 A1 May 12, 2011

Related U.S. Application Data

(60) Provisional application No. 61/259,403, filed on Nov. 9, 2009.

(51) Int. Cl.
*A61K 9/16* (2006.01)

(52) U.S. Cl.
USPC ............ 424/489; 424/464; 424/474; 424/479

(58) Field of Classification Search
USPC ................................ 424/465–490
See application file for complete search history.

(56) References Cited

U.S. PATENT DOCUMENTS

| | | | |
|---|---|---|---|
| 6,002,008 A | 12/1999 | Wissner et al. | |
| 6,288,082 B1 | 9/2001 | Wissner et al. | |
| 6,297,258 B1 * | 10/2001 | Wissner et al. | 514/313 |
| 6,384,051 B1 | 5/2002 | Frost et al. | |
| 7,399,865 B2 | 7/2008 | Wissner et al. | |
| 2006/0128793 A1 * | 6/2006 | Zask et al. | 514/453 |
| 2008/0268034 A1 | 10/2008 | Karanth et al. | |
| 2009/0203709 A1 * | 8/2009 | Steinberg et al. | 514/252.18 |

FOREIGN PATENT DOCUMENTS

| | | |
|---|---|---|
| WO | WO2005/037287 | 4/2005 |
| WO | WO 2005037287 A1 * | 4/2005 |
| WO | WO2006/116514 | 11/2006 |
| WO | WO2007/130438 | 11/2007 |
| WO | WO2008/089087 | 7/2008 |
| WO | WO2008/093878 | 8/2008 |
| WO | WO2011/002857 | 1/2011 |

OTHER PUBLICATIONS

Boyce, B., et al., "Requirement of pp60$^{c\text{-}src}$ Expression for Osteoclasts to Form Ruffled Borders and Resorb Bone in Mice," *Clinical Investigation*, 1992, 1622-1627, vol. 90.
Bridges, A., "Current Progress Towards the Development of Tyrosine Kinase Inhibitors As Anticancer Agents," *Emerging Drugs: The Prospect for Improved Medicines*, 1998, 279-292, vol. 3.
Folkman, J., "Angiogenesis in Cancer, Vascular, Rheumatoid and Other Disease,"*Nature Medicine*, 1995, 27, vol. 1, No. 1.
Good, W., "A Comparison of Contact Angle Interpretations," *Journal of Colloid and Interface Science*, 1973, 63-71, vol. 44, No. 1.
Janczuk, B., et al., "Surface Free-Energy Components of Liquids and Low Energy Solids Land Contact Angles," *Journal of Colloid AndInterface Science*, 1989, 189-204, vol. 127.
Jasper, J., "The Surface Tension of Liquid," *J. Phys. Chem. Ref. Data*, 1972, 859, vol. 1, No. 4.
Mattsson, E., et al., "Current Concepts in Restenosis Following Balloon Angioplasty," *Trends Cardiovascular Medicine*, 1995, 200-204,vol. 5.
Raines, E., et al., "Multiple Growth Factors Are Associated With Lesions of Atherosclerosis: Specificity or Redundancy?" *BioEssays*, 1996, 271-282, vol. 18, No. 4.
Shaw, K., et al., "Pharmacological Inhibition of Restenosis: Learning From Experience," *Trends Pharmacological Science*, 1995, 401-404, vol. 16.
Shawver, L., et al., "Receptor Tyrosine Kinases As Targets for Inhibition of Angiogenesis," *Drug Discovery Today*, 1997, 50-63, vol. 2.
Traxler, P., "Tyrosine Kinase Inhibitors in Cancer Treatment (Part II)" *Expert Opinion on Therapeutic Patents*, 1998, 1599-1625, vol. 8, No. 12.

* cited by examiner

*Primary Examiner* — Michael G Hartley
*Assistant Examiner* — Micah-Paul Young
(74) *Attorney, Agent, or Firm* — Jones Day

(57) ABSTRACT

The present invention provides coated tablet formulations comprising neratinib maleate, and improved methods for making such coated tablets.

18 Claims, 1 Drawing Sheet

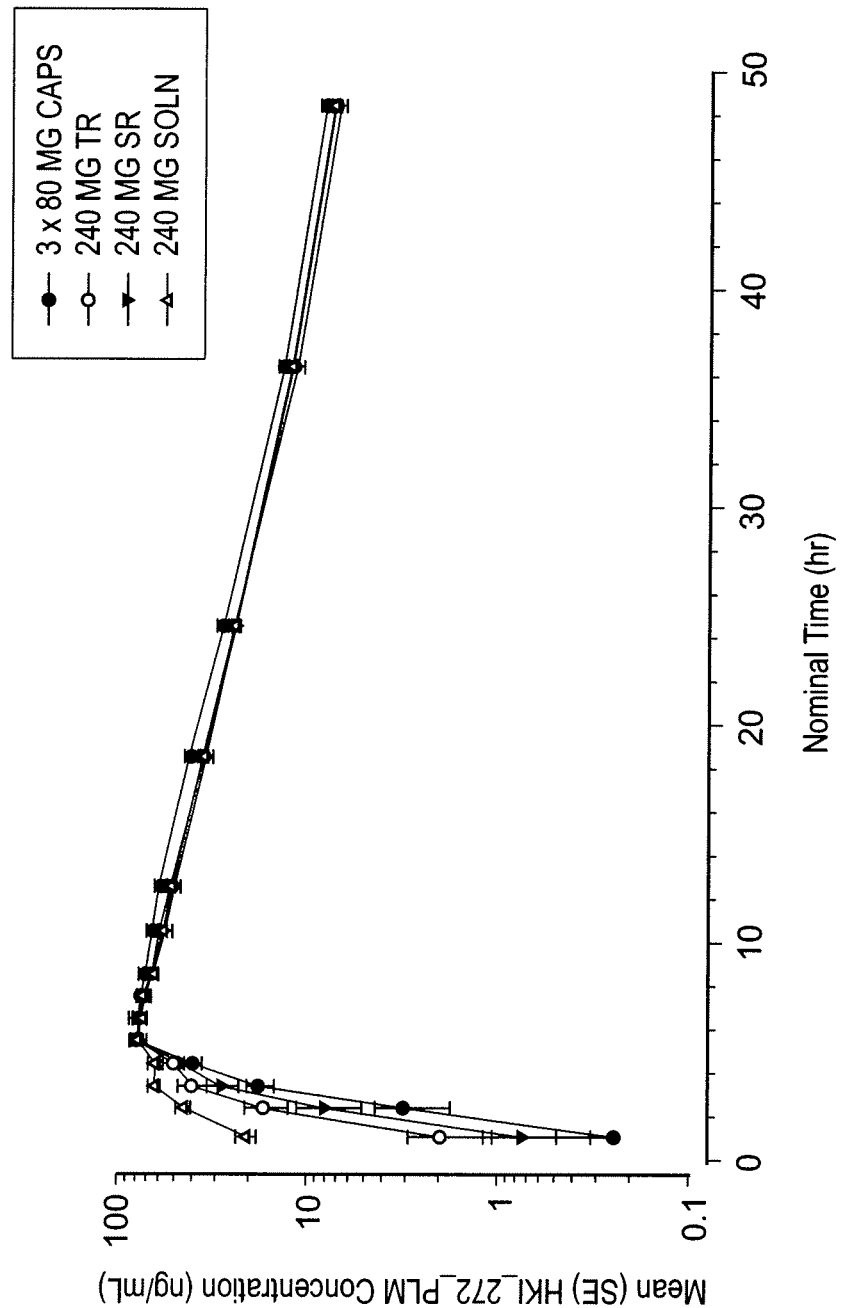

US 8,518,446 B2

COATED TABLET FORMULATIONS AND USES THEREOF

CROSS-REFERENCE TO RELATED APPLICATIONS

This application claims the benefit of U.S. Application No. 61/259,403, filed Nov. 9, 2009, which is hereby incorporated by reference in its entirety.

FIELD OF THE INVENTION

The present invention relates to oral pharmaceutical formulations of neratinib provided in the form of coated tablets prepared by fluid bed granulation or by wet granulation, and improved methods of making these coated tablets.

BACKGROUND OF THE INVENTION

Protein kinases are important in the transmission of biochemical signals, which initiate cell replication. Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration. Specific protein kinases have been implicated in adverse conditions including cancer [Traxler, P. M., *Exp. Opin. Ther. Patents*, 8, 1599 (1998); Bridges, A. J., *Emerging Drugs*, 3, 279 (1998)], restenosis [Mattsson, E., *Trends Cardiovas. Med.* 5, 200 (1995); Shaw, *Trends Pharmacol. Sci.* 16, 401 (1995)], atherosclerosis [Raines, E. W., *Bioessays*, 18, 271 (1996)], angiogenesis [Shawver, L. K., *Drug Discovery Today*, 2, 50 (1997); Folkman, J., *Nature Medicine*, 1, 27 (1995)] and osteoporosis [Boyce, *J. Clin. Invest.*, 90, 1622 (1992)]. Compounds capable of inhibiting the activity of receptor tyrosine kinases are known to be useful in the treatment of cancers, including but not limited to for example, non-small cell lung cancer (NSCLC), breast cancer, polycystic kidney disease, colonic polyps, and stroke in mammals. A specific kinase inhibitor is (E)-N-(4-(3-chloro-4-(pyridin-2-ylmethoxy)phenylamino)-3-cyano-7-ethoxyquinolin-6-yl)-4-(dimethylamino)but-2-enamide, also known as neratinib. Nerartinib is a weak base having low bioavailability and low solubility in both water and alcohol.

Neratinib maleate particles exhibit very high surface free energy, (work of cohesion=45.62 mN/m). This property renders the primary particles very cohesive and prone to aggregation as described by B. Janczuk and T. Bialopiotrowicz, "Surface Free-Energy Components of Liquids and Low Energy Solids and Contact Angles," in J. Colloid Interf. Sci. 127 (1989), p. 189-204; W. R. Good, "A Comparison of Contact Angle Interpretations," in J. Colloid Interf. Sci. 44 (1973), p. 63; M. D. Lechner (Ed.), Landolt Börnstein, New Series, Vol. IV/16, "Surface Tension of Pure Liquids and Binary Liquid Mixture," Springer Verlag, 1998; and J. J. Jasper, "The Surface Tension of Pure Liquid Compounds," in J. Phys. Chem. Ref. Data, Vol. 1, No. 4, 1972, p. 859. As a consequence of cohesiveness, neratinib maleate powder does not lend itself easily to pharmaceutical operations such as mixing, flow or fluidization especially when it constitutes a high proportion in a composition. Due to these limitations, it was not possible to develop a neratinib maleate formulation comprising a capsule or tablet of higher strength employing a direct compression or roller compaction processes successfully. A formulation using a conventional wet granulation method led to chemical degradation and stability issues.

SUMMARY OF THE INVENTION

It is desirable to provide a neratinib maleate formulation, where the surface property of the active ingredient is modified by spraying or otherwise applying a substance, such as a polymer like povidone, of low surface energy (for instance about 38 mN/m) on the surface of neratinib maleate particles.

The present invention provides pharmaceutically acceptable solid compositions suitable for oral administration comprising the active ingredient neratinib maleate. In certain embodiments, such solid compositions are provided in the form of coated tablets prepared by fluid bed granulation. In some embodiments, the present invention provides a unit dosage form comprising neratinib maleate.

The present invention provides a pharmaceutically acceptable composition comprising: a granulation comprising intragranular components: (a) 10-70 weight percent neratinib maleate; (b) 15-65 weight percent of one or more fillers; (c) 0-8 or 0.5-8 weight percent of one or more disintegrants; and (d) 0.2-8 weight percent, in certain embodiments 0.2-6 weight percent, of one or more glidants; and (e) 5-15 weight percent of one or more surface modifying agents. The granulation is combined with extragranular components (f) 1-25 or 4-25 weight percent of one or more fillers; (g) 1-8 or 0-8 weight percent of one or more disintegrants and (h) 0.1-3 or 0.5-3 weight percent of one or more lubricants, and then compressed into tablets or dry-filled into capsules.

The present invention provides a pharmaceutically acceptable composition comprising: a granulation comprising intragranular components (a) 10-70 weight percent of neratinib maleate; (b) 15-65 weight percent of mannitol and microcrystalline cellulose; (c) 0.5-8 weight percent of crospovidone or croscarmellose sodium; and (d) 0.2-8 weight percent, in certain embodiments 0.2-6 weight percent, of colloidal silicon dioxide, and (e) 5-15 weight percent of povidone. The granulation is combined with extragranular components (f) 1-25 or 4-25 weight percent of microcrystalline cellulose; (g) 0-8 or 1-80-8 weight percent of crospovidone or croscarmellose sodium and (h) 0.1-3 or 0.5-3 weight percent of magnesium stearate, and then compressed into tablets or dry-filled into capsules.

The present invention also provides methods of preparing stable, pharmaceutically acceptable neratinib-maleate formulations for oral administration comprising components described above and herein, which allow for improved processing characteristics while maintaining acceptable pharmokinetic properties.

BRIEF DESCRIPTION OF THE DRAWINGS

FIG. 1 summarizes mean pharmacokinetic parameters versus time for neratinib maleate following the administration of immediate release tablet formulations of neratinib with different dissolution rates. TR refers to a rapid dissolving tablet, while SR dissolve relatively slowly. The presented data shows plasma concentration levels following administration of a single oral dose (240-mg tablet) in subjects.

DETAILED DESCRIPTION OF CERTAIN EMBODIMENTS OF THE INVENTION

1. Definitions

As used herein, an "effective amount" of a compound or pharmaceutically acceptable composition can achieve a desired therapeutic and/or prophylactic effect. In some embodiments, an "effective amount" is at least a minimal amount of a compound, or composition containing a compound, which is sufficient for treating one or more symptoms of a disorder or condition associated with modulation of protein tyrosine kinases. In certain embodiments, an "effective amount" of a compound, or composition containing a compound, is sufficient for treating symptoms associated with, a disease associated with an aberrant tyrosine kinase receptor (e.g. cancer, including malignant and benign tumor growths).

The term "subject", as used herein, means a mammal and includes human and animal subjects, such as domestic animals (e.g., horses, dogs, cats, etc.).

The terms "suffer" or "suffering" as used herein refers to one or more conditions that a patient has been diagnosed with, or is suspected to have.

The terms "treat" or "treating," as used herein, refers to partially or completely alleviating, inhibiting, delaying onset of, preventing, ameliorating and/or relieving a disorder or condition, or one or more symptoms of the disorder or condition.

"Therapeutically active agent" or "active agent" refers to a substance, including a biologically active substance, that is useful for therapy (e.g., human therapy, veterinary therapy), including prophylactic and therapeutic treatment. Therapeutically active agents include organic molecules that are drug compounds, peptides, proteins, carbohydrates, monosaccharides, oligosaccharides, polysaccharides, nucleoprotein, mucoprotein, lipoprotein, synthetic polypeptide or protein, small molecules linked to a protein, glycoprotein, steroid, nucleic acid, DNA, RNA, nucleotide, nucleoside, oligonucleotides, antisense oligonucleotides, lipid, hormone, and vitamin. Therapeutically active agents include any substance used as a medicine for treatment, prevention, delay, reduction or amelioration of a disease, condition, or disorder. Among therapeutically active agents useful in the formulations of the present invention are opioid receptor antagonist compounds, opioid analgesic compounds, and the like. Further detailed description of compounds useful as therapeutically active agents is provided below. A therapeutically active agent includes a compound that increases the effect or effectiveness of a second compound, for example, by enhancing potency or reducing adverse effects of a second compound.

"Unit dosage form" as used herein refers to a physically discrete unit of inventive formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

In dry granulation (slugging or roller compaction) intragranular materials are blended to prepare slugs or roller compaction. Material is milled and blended with extragranular materials followed by capsule filling or tablet 20 compression. Wet granulation entails blending intragranular materials. Wet granulate the blend with water, with or without a binder, (using high sheer, low sheer granulators) and dry (using temperatures up to 100° C.). Material is milled and blended with extragranular materials followed by capsule filling or tablet compression. See, 25 Handbook of Pharmaceutical Granulation Technology, 1997, Dilip Parikh, Marcel Dekker, Inc. ISBN 0-8247-9882-1, pages 338-368.

2. Pharmaceutically Acceptable Compositions and Formulations

In certain embodiments, the present invention provides a pharmaceutically acceptable composition for intravenous administration comprising: neratinib maleate. Neratinib and other 4-amino-3-cyanoquinoline compounds are disclosed in U.S. Pat. Nos. 6,002,008, 6,288,082, 6,297,258, 6,384,051 and 7,399,865. Neratinib has the following chemical structure:

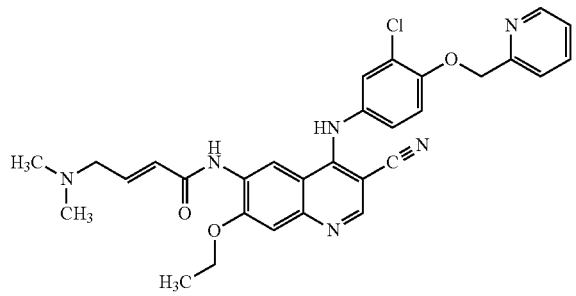 [SMILES: CCOc1cc2ncc(C#N)c(Nc3ccc(OCc4ccccn4)c(Cl)c3)c2cc1NC(=O)/C=C/CN(C)C]

and is isolated as a free base or prepared as a pharmaceutically acceptable salt, such as a maleate salt. Neratinib is a weak base with an intrinsic low solubility in water.

In certain embodiments, solid pharmaceutically acceptable compositions of neratinib maleate are provided in the form of tablets prepared by fluid bed granulation. Intragranular particulate components comprising an active ingredient, namely neratinib maleate, one or more fillers, a disintegrant and a glidant are sprayed with, or otherwise wholly or partially covered with, a surface modifying agent, such as povidone, to lower the surface energy of the particles. The fluid bed process is employed to effectively modify the surface behavior of the particulate active ingredient, so that any water instantly dries and does not bring about any polymorphic or chemical change in active during the process. The surface property of the active ingredient is modified by spraying a polymer, for instance povidone, having a low surface energy (for instance of about 38 mN/m) on the surface of the intragranular particles. After the modification of surface properties, the intragranular particles are no longer cohesive, or are significantly less cohesive, and are easily rendered to all pharmaceutical operations. The surface-modified intragranular particles are then further processed, typically by combining with extragranular components typically comprising a filler, a disintegrant and a lubricant, and further processed into dry-filled capsules or tablets for oral administration. The surface modified intragranular components can also be used directly to make dosage forms without combination with extragranular components, for instance in connection with dry-filled capsules.

In certain embodiments, solid pharmaceutically acceptable compositions of neratinib maleate are provided in the form of tablets prepared by wet granulation. Increasing the glidant and lubrication levels provided an improved neratinib maleate formulation that flowed without aggregation of granules, as compared to a wet granulated neratinib maleate formulation used in clinical trials. The glidant was increased from 0.5% to 2.0% to improve the flow of the pre-blended material. The picking and sticking issues observed during compression were eliminated by increasing the lubrication level from 0.5% to 3.0%, in certain embodiments 0.5% to 2.0%. In certain embodiments the amount of lubricant such as magnesium stearate needed is as low as 0.2% or even 0.1%. The increase in amount of glidant and lubricant was compensated by a corresponding reduction in the amount of fillers added to the formulation.

In some embodiments, the active ingredient comprises a 4-amino-3-cyanoquinoline compound such as neratinib, specifically neratinib maleate, or a pharmaceutically acceptable salt thereof. Suitable examples of 4-amino-3-cyanoquinoline compounds are disclosed in U.S. Pat. Nos. 6,002,008, 6,288,082, 6,297,258, 6,384,051 and 7,399,865. According to one embodiment, neratinib maleate is the active ingredient. The active ingredient comprises from about 10 weight % to about 70 weight %, including from 20-50 weight % and about 35 weight % or 41 weight %, based upon total weight of the formulation.

According to one embodiment, a surface modifying agent is sprayed onto particulate intragranular components before further processing with extragranular components. Suitable surface modifying agents include, but are not limited to for example, povidone, gelatin, starch, hydroxy propyl methyl cellulose and hydroxy propyl cellulose. In one embodiment, povidone is the surface modifying agent. The surface modifying agent comprises from about 1 weight % to about 15 weight %, including from 3-12 weight % and from 5-10 weight %, based upon total weight of the formulation.

Suitable fillers (also referred to as "diluents") are known in the art. For example, suitable fillers include but are not limited to starch, dextrin, sucrose, Sorbitol, Sodium Saccharin, Acesulfame potassium, Xylitol, Aspartame, Mannitol, starch, PVP (polyvinyl pyrrolidone), low molecular weight HPC (hydroxypropyl cellulose), microcrystalline cellulose (MCC), low molecular weight HPMC (hydroxypropyl methylcellulose), low molecular weight carboxymethyl cellulose, ethylcellulose, dicalcium phosphate, silicified microcrystalline cellulose, alginates, gelatin, polyethylene oxide, acacia, dextrin, sucrose, magnesium aluminum silicate, and polymethacrylates. Fillers include agents selected from the group consisting of microcrystalline cellulose, starch, lactitol, lactose, a suitable inorganic calcium salt, sucrose, glucose, mannitol, silicic acid, or a combination thereof. The fillers, as an intragranular component, comprise from about 15 weight % to about 65 weight %, based upon total weight of the formulation. In one embodiment, the intragranular filler is a combination of mannitol and microcrystalline cellulose. The fillers, as an extragranular component, comprise from about 4 weight % to about 25 weight %, based upon total weight of the formulation. In one embodiment, the extragranular filler is microcrystalline cellulose.

Suitable disintegrants are known in the art and include but are not limited to, agar, calcium carbonate, potato or tapioca starch, alginic acid, certain silicates, sodium carbonate, crospovidone (cross-linked PVP), sodium carboxymethyl starch (sodium starch glycolate), cross-linked sodium carboxymethyl cellulose (croscarmellose), pregelatinized starch (starch 1500), microcrystalline starch, water insoluble starch, sodium starch glycolate, potassium polacrilin, sodium alginate, calcium carboxymethyl cellulose, magnesium aluminum silicate (Veegum) or a combination thereof. In some embodiments, a disintegrant is crospovidone. The disintegrant, as an intragranular component, comprises from about 0 or 0.5 weight % to about 8 weight %, including from 0 or 0.5-6 weight % and from 0 or 0.5-50-5 weight %, based upon total weight of the formulation. The disintegrant, as an extragranular component, comprises from about 0 or 1 weight % to about 8 weight %, based upon total weight of the formulation.

A glidant is used as an intragranular component of the formulation. Suitable glidants include, without limitation, colloidal silicon dioxide, talc, magnesium carbonate, calcium silicate, fumed silicon dioxide, and combinations thereof. In some embodiments, the glidant is colloidal silicon dioxide. The amount of glidants used is 0.2-8 weight percent, or 0.2-5 weight percent, including 0.5-2 weight %, based on the total weight of the formulation.

A lubricant is used as an extragranular component of the formulation. Suitable lubricants or glidants include for example stearates, sodium stearyl fumarate, magnesium salts and magnesium stearate. In some embodiments, the lubricant is magnesium stearate. The amount of lubricants used is 0.2-4 weight percent, in certain embodiments 0.5-3 weight %, based on the total weight of the formulation.

Provided compositions may be formulated into a unit dosage form. Such formulations are well known to one of ordinary skill in the art. In certain embodiments, the present invention provides a formulation comprising a solid dosage form as a tablet. In other embodiments, the present invention provides a solution for oral administration. In some embodiments, a unit dosage form contains 5, 10, 20, 25, 40, 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1025 mg, 1050 mg, 1075 mg, 1100 mg, 1125 mg, 1150 mg, 1175 mg, 1200 mg, 1225 mg, 1250 mg, 1275 mg, 1300 mg, 1325 mg, 1350 mg, 1375 mg, 1400 mg, 1425 mg, 1450 mg, 1475 mg, 1500 mg of neratinib In some embodiments, a unit dosage form contains between 5 mg and 500 mg, inclusive, or between 10 mg and 450 mg, inclusive, of neratinib. In some embodiments, a unit dosage form contains 40 mg, 80 mg, 100 mg, 120 mg, 240 mg, 360 mg, or 480 mg. In some embodiments, a unit dosage form contains more than 500 mg of neratinib.

In some embodiments, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

For the treatment of cancer, the inventive formulations of this invention can be administered in combination with other anti-tumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, anti-metabolites such as 5-fluorouracil or hydroxyurea, DNA intercalators such as adriamycin or bleomycin, topoisomerase inhibitors such as etoposide or camptothecin, antiangiogenic agents such as angiostatin, and anti-estrogens such as tamoxifen.

Based on the results disclosed for neratinib and other 4-amino-3-cyanoquinoline compounds in U.S. Pat. No. 6,297,258, the invented formulations are useful antineoplastic agents of significant efficacy, which are useful in treating, inhibiting the growth of, or eradicating neoplasms. In particular, the compounds of this invention are useful in treating, inhibiting the growth of, or eradicating neoplasms that express the receptor protein produced by the erbB2 (Her2) oncogene.

3. Combination Products and Combined Administration

In certain embodiments, inventive compositions, and formulations thereof, may be administered alone to treat one or more disorders as described herein, or alternatively may be administered in combination with (whether simultaneously or sequentially) one or more other active agents useful to treat one or more disorders as described herein. Thus, an inventive composition, or formulation thereof, can be administered concurrently with, prior to, or subsequent to, one or more active agents.

In certain embodiments, inventive compositions include one or more other active agents in addition to neratinib that is not neratinib. In some embodiments, inventive formulations comprise both another anticancer compound and neratinib.

The amount of additional active agent(s) present in combination compositions of this invention will typically be no more than the amount that would normally be administered in a composition comprising that active agent as the only therapeutic agent. In certain embodiments of the present invention, the amount of additional active agent will range from about 50% to 100% of the amount normally present in a composition comprising that compound as the only therapeutic agent.

4. Uses and Kits of Inventive Compositions

Provided compositions, and formulations thereof, are also useful in treatment of conditions including cancers.

In still further embodiments, veterinary applications (e.g., treatment of domestic animals, e.g. horse, dogs, cats, etc.) of use of inventive compositions, and formulations thereof, are provided. Thus, use of provided formulations in veterinary applications analogous to those discussed above for human subjects is contemplated.

It will also be appreciated that inventive compositions, and formulations thereof, can be employed in combination therapies, that is, an inventive composition, or formulation thereof, can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, inventive compositions, and formulations thereof, and unit dose forms are useful in preparation of medicaments, including, but not limited to medicaments useful in the treatment of cancer.

Still further encompassed by the invention are pharmaceutical packs and/or kits comprising inventive compositions, and formulations thereof, and a container (e.g., a foil or plastic package, or other suitable container). Optionally instructions for use are additionally provided in such kits.

In order that the invention described herein may be more fully understood, the following examples are set forth. It should be understood that these examples are for illustrative purposes only and are not to be construed as limiting this invention in any manner.

All features of each of the aspects of the invention apply to all other aspects mutatis mutandis.

EXAMPLES

Example 1

Preparation of Coated Tablets of a Neratinib Maleate Formulation by Fluid Bed Wet Granulation Process A pharmaceutically acceptable formulation of neratinib mealate is prepared: a granulation comprising intragranular components (a) 10-70 weight percent of neratinib maleate; (b) 15-65 weight percent of mannitol and microcrystalline cellulose; (c) 0.5-8 weight percent of crospovidone or crosscarmellose sodium; (d) 0.2-8 weight percent of colloidal silicon dioxide, and (e) 5-15 weight percent of povidone. The granulation is combined with extragranular components (f) 4-25 weight percent of microcrystalline cellulose; (g) 1-8 weight percent of crospovidone and (h) 0.5-3 weight percent of magnesium stearate, and then compressed into tablets or dry-filled into capsules. This and certain preferred ranges of materials are shown below in Table 1.

TABLE 1

| Component | Weight % | Weight % range | Weight % range |
|---|---|---|---|
| Intra-granular components | | | |
| HKI-272 Maleate, anhydrous | 41 | 20-50 | 10-70 |
| Mannitol | | | 15-65 |
| Microcrystalline cellulose, | | | 5-35 |
| Crospovidone/croscarmellose sodium | 0.5-5.00 | 2-6 | 0.5-8 |
| Povidone | 5-10 | 3-12 | 1-15 |
| Colloidal Silicon Dioxide | 0.5-2.0 | 0.2-3 | 0.2-5 |
| Extra-granular components | | | |
| Microcrystalline cellulose | 4-25 | 4-25 | 4-25 |
| Crospovidone/carmellose sodium | 1-8 | 1-8 | 1-8 |
| Magnesium stearate | 0.5-3.0 | 0.2-3.5 | 0.2-4.0 |
| Total (Core Tablet) | 1.1.1 | 1.1.2 | 1.1.3 |
| Film coat: | | | |
| Opadry ® | | | |

The formulation was prepared according to the following procedure:
1. Mixed neratinib maleate, mannitol, microcrystalline cellulose and crospovidone and silicon dioxide. Any diffusive or convective mixer may be used.
2. Dissolved povidone in purified water.
3. Fluidized the powder blend in step 1 and sprayed it with solution prepared in step 2 in a suitable fluid bed granulator and dryer.
4. Dried the granulation.
5. Milled the granulation.
6. Added microcrystalline cellulose and crospovidone to the granulation in step 5 and mixed.
7. Added magnesium stearate to the mixture in step 6 and mixed.
8. Compressed the blend in step 7 into tablets of desired strength.

9. Applied film-coat to compressed tablets using Opadry II of desired color.
10. Alternatively the powder blend can be filled in capsules shells.

Example 2

Unit Dosage Forms of an Exemplary Neratinib Maleate Formulation

Using the fluid bed process described in Example 1, different unit dosages of neratinib maleate were prepared from an exemplary formulation, as summarized in Table 2.

TABLE 2

| Ingredient | Function | Granulation wt/wt (%) | 40 mg mg/tablet | 80 mg Mg/tablet | 240 mg mg/tablet |
|---|---|---|---|---|---|
| Intragranular Components | | | | | |
| HKI-272 Maleate[a] | Active | 35.00 | 40.00 | 80.00 | 240.00 |
| Mannitol (Pearlitol 200 SD) | Diluent | 38.94 | 44.50 | 89.01 | 267.02 |
| Microcrystalline (Avicel PH 101) | Diluent | 10.56 | 12.07 | 24.14 | 72.41 |
| Crospovidone | Disintegrant | 3.00 | 3.43 | 6.86 | 20.57 |
| Povidone USP/K-25 | Surface Modifying Agent | 5.00 | 5.71 | 11.43 | 34.29 |
| Colloidal SiO2 | Glidant | 2.00 | 2.29 | 4.57 | 13.71 |
| Extragranular Components | | | | | |
| Avicel PH 101 | Diluent | 1.50 | 1.71 | 3.43 | 10.29 |
| Crospovidone | Disintegrant | 2.00 | 2.29 | 4.57 | 13.71 |
| Mg Stearate | Lubricant | 2.00 | 2.29 | 4.57 | 13.71 |
| Total Wt. | | 100.00 | 114.29 | 228.57 | 685.71 |
| Film Coating: | | | | | |
| Opadry II (85F15443) Red | Film Coat | — | 3.429 (3%) | — | — |
| Opadry II (85F92177) Yellow | Film Coat | — | — | 6.86 (3%) | — |
| Opadry II (85F94211) Pink | Film Coat | — | — | — | 20.57 (3%) |
| Total Tablet Wt | | — | 117.714 | 235.43 | 706.28 |

[a]Weight percent as HKI-272 free base.

Example 3

Coated Tablets of Targeted Release Neratinib Maleate Manufactured by Spraying Povidone on Intragranular Components in a Fluid Bed An exemplary targeted release (TR) neratinib maleate formulation is summarized in Table 3.

TABLE 3

| Ingredient | % wt/wt | 40 mg Tablet (mg) | 240 mg Tablet (mg) | Function |
|---|---|---|---|---|
| Intragranular Components | | | | |
| HKI-272 Maleate, anhydrous | 35.00 | 40.0 | 240.00 | Active |
| Mannitol | 38.25 | 43.79 | 262.72 | Filler |
| Microcrystalline cellulose, | 12.75 | 14.50 | 86.99 | Filler |
| Crospovidone | 3.00 | 3.43 | 20.57 | Disintegrant |
| Povidone | 5.00 | 5.71 | 34.29 | Surface Modifying Agent |
| Colloidal Silicon Dioxide | 0.50 | 0.57 | 3.43 | Glidant |
| Extra-granular Components | | | | |
| Microcrystalline cellulose | 3.00 | 3.43 | 20.57 | Filler |
| Crospovidone | 2.00 | 2.29 | 13.71 | Disintegrant |
| Magnesium stearate | 0.50 | 0.57 | 3.43 | Lubricant |
| Total (Core Tablet) | 100.00 | 114.29 | 685.71 | |
| Film coat: | | | | |
| Opadry ® | | 3.43 | 20.57 | Film coat |

Example 4

Coated Tablets of Slow Release Neratinib Maleate Manufactured by Spraying Povidone on Intragranular Components in a Fluid Bed An exemplary slow release (SR) neratinib maleate formulation is summarized in Tables 4A and 4B.

TABLE 4A

| Ingredient Name | Function | % Wt/Wt | mg/tablet 240 mg Tablet |
|---|---|---|---|
| Intra-granular Components | | | |
| HKI-272 maleate | Active | 35.00 | 240.00 |
| Mannitol USP | Filler | 41.81 | 286.69 |
| Microcrystalline Cellulose NF | Filler | 9.19 | 63.02 |
| Crospovidone NF | Disintegrant | 0 | |
| Colloidal Silicon Dioxide, NF | Glidant | 0.50 | 3.43 |
| Povidone USP/K-25 | Binder | 10.00 | 68.57 |
| Purified Water, EP/BP/USP | Solvent | — | |
| Extra-granular Components | | | |
| Microcrystalline Cellulose NF | Filler | — | |
| Crospovidone NF | Disintegrant | 0.50 | 3.43 |
| Magnesium Stearate, NF/Ph/ EU. (Vegetable grade), | Lubricant | 3.00 | 20.57 |

TABLE 4B

| Ingredient | Function | Granulation wt/wt (%) | 40 mg mg/tablet | 80 mg Mg/tablet | 240 mg mg/tablet |
|---|---|---|---|---|---|
| Intragranular Components | | | | | |
| HKI-272 Maleate | Active | 35.00 | 40.00 | 80.00 | 240.00 |
| Mannitol (Pearlitol 200 SD) | Diluent | 38.94 | 44.50 | 89.01 | 267.02 |
| Microcrystalline (Avicel PH 101) | Diluent | 10.56 | 12.07 | 24.14 | 72.41 |
| Croscarmellose sodium | Disintegrant | 3.00 | 3.43 | 6.86 | 20.57 |
| Povidone USP/K-25 | Surface Modifying Agent | 5.00 | 5.71 | 11.43 | 34.29 |
| Colloidal SiO2 | Glidant | 2.00 | 2.29 | 4.57 | 13.71 |
| Extragranular Components | | | | | |
| Avicel PH 101 | Diluent | 1.50 | 1.71 | 3.43 | 10.29 |
| Croscarmellose sodium | Disintegrant | 2.00 | 2.29 | 4.57 | 13.71 |
| Mg Stearate | Lubricant | 2.00 | 2.29 | 4.57 | 13.71 |
| Total Wt. | | 100.00 | 114.29 | 228.57 | 685.71 |
| Film Coating: | | | | | |
| Opadry II (85F15443) Red | Film Coat | — | 3.429 (3%) | — | — |
| Opadry II (85F92177) Yellow | Film Coat | — | — | 6.86 (3%) | — |
| Opadry II (85F94211) Pink | Film Coat | — | — | — | 20.57 (3%) |
| Total Tablet Wt | — | | 117.714 | 235.43 | 706.28 |

Example 5

Drug Release Data

Drug release data are summarized for neratinib maleate formulations in Examples 3 and 4, as summarized in Table 5. Dissolution of tablets was carried out employing 900 ml of 0.1N HCl as dissolution medium in USP dissolution apparatus 2, and a paddle speed of 50±1 rpm at 37±0.5° C. Samples were taken at specific time points and were analyzed by UV spectrometer at 266 nm.

TABLE 5

Dissolution data for Neratinib Maleate Formulations

| | % Dissolved | |
|---|---|---|
| Time (minutes) | TR Tablet Formulation | SR Tablet Formulation |
| 15 | 47 | 24 |
| 30 | 83 | 43 |
| 45 | 99 | 64 |
| 60 | 99 | 82 |

Mean pharmacokinetic parameters for neratinib maleate in targeted release and slow release formulations following administration of a single oral dose (240-mg tablet) in subjects were evaluated and summarized in Table 6. The mean concentration versus time profiles for targeted release and slow release formulations are summarized in FIG. 1.

TABLE 6

Summary of Mean Pharmacokinetic Parameters for Neratinib Maleate Formulations Following Single Oral Dose (240-mg tablet) in Healthy Subjects Under Fed Conditions

| Mean ± SD (CV %) [Geometric Mean] | 240 mg TR (n = 26) | 240 mg SR (n = 26) |
|---|---|---|
| $C_{max}$ (ng/mL) | 81.38 ± 27.49 (34) [77.13] | 82.21 ± 29.73 (36) [77.12] |
| $t_{max}$ (hr) | 5.00 (3.00, 12.00) | 6.00 (3.00, 12.00) |
| AUC | 1432 ± 450 (31) [1358] | 1474 ± 467 (32) [1393] |

What is claimed is:

1. A pharmaceutically acceptable composition comprising: a granulation comprising intragranular components: (a) 10-70 weight percent neratinib maleate; (b) 15-65 weight percent of one or more fillers; (c) 0-8 weight percent of one or more disintegrants; (d) 0.2-8 weight percent of one or more glidants; and (e) 5-15 weight percent of one or more surface modifying agents; wherein the granulation is combined with extragranular components: (f) 1-25 weight percent of one or more fillers; (g) 0-8 weight percent of one or more disintegrants; and (h) 0.1-3 weight percent of one or more lubricants.

2. A pharmaceutically acceptable composition comprising intragranular components: 10-70 weight percent of neratinib maleate and 5-15 weight percent of povidone; and extragranular components: microcrystalline cellulose, crospovidone and magnesium stearate.

3. A pharmaceutically acceptable composition comprising intragranular components: (a) 10-70 weight percent of neratinib maleate; (b) 15-65 weight percent of mannitol, microcrystalline cellulose or a combination of both; (c) 0.5-8 weight percent crospovidone, croscarmellose sodium or a combination of both; (d) 0.2-8 weight percent colloidal silicon dioxide; and (e) 5-15 weight percent povidone; and extragranular components: (f) 1-25 weight percent of microcrystalline cellulose; (g) 1-8 weight percent of crospovidone; and (h) 0.5-3 weight percent of magnesium stearate.

4. A tablet comprising the composition of claim 3.

5. A dry-filled capsule comprising the composition of claim 3.

6. The composition according to claim 3, wherein the amount of neratinib maleate is about 41 weight percent.

7. The composition according to claim 3, wherein the amount of mannitol and microcrystalline cellulose, as an intragranular component, is about 50 weight percent.

8. The composition according to claim 3, wherein the amount of crospovidone, as an intragranular component, is about 3 weight percent.

9. The composition according to claim 3, wherein the amount of povidone, as an intragranular component, is about 5 weight percent.

10. The composition according to claim 3, in the form of an oral dosage of 40 mg, 80 mg, or 240 mg.

11. A method for preparing a pharmaceutically acceptable composition, comprising: (1) spraying 5-15 weight percent of one or more surface modifying agents onto intragranular components of a granulation, said intragranular components comprising: (a) 10-70 weight percent neratinib maleate; (b) 15-65 weight percent of one or more fillers; (c) 0-8 weight percent of one or more disintegrants; and (d) 0.2-8 weight percent of one or more glidants; and (2) combining said coated intragranular components with extragranular components of the granulation, said extragranular components comprising: (e) 1-25 weight percent of one or more fillers; (f) 0-8 weight percent of one or more disintegrants; and (g) 0.1-3 weight percent of one or more lubricants.

12. The method according to claim 11, wherein the surface modifying agent is povidone.

13. A method for treating cancer comprising administering an effective amount of a composition according to claim 1; wherein the cancer results from an aberrant tyrosine kinase receptor.

14. The composition according to claim 3, wherein the amount of colloidal silicon dioxide, as an intragranular component, is about 2 weight percent.

15. The composition according to claim 3, wherein the amount of neratinib maleate is about 35 weight percent.

16. The pharmaceutically acceptable composition of claim 3, comprising intragranular components: (a) 10-70 weight percent of neratinib maleate; (b) 15-65 weight percent of mannitol and microcrystalline cellulose; (c) 0.5-8 weight percent of crospovidone; (d) 0.2-8 weight percent of colloidal silicon dioxide; and (e) 5-15 weight percent of povidone; and extragranular components: (f) 1-25 weight percent of microcrystalline cellulose; (g) 1-8 weight percent of crospovidone; and (h) 0.5-3 weight percent of magnesium stearate.

17. The pharmaceutically acceptable composition of claim 3, comprising intragranular components: (a) 35 weight percent of neratinib maleate; (b) about 50 weight percent of mannitol and microcrystalline cellulose; (c) 3 weight percent of crospovidone; (d) 2 weight percent of colloidal silicon dioxide; and (e) 5 weight percent of povidone; and extragranular components: (f) 1.5 weight percent of microcrystalline cellulose; (g) 2 weight percent of crospovidone; and (h) 2 weight percent of magnesium stearate.

18. The pharmaceutically acceptable composition of claim 3, comprising 40 mg of neratinib maleate.

\* \* \* \* \*